US011832567B2

(12) United States Patent
Lei et al.

(10) Patent No.: US 11,832,567 B2
(45) Date of Patent: Dec. 5, 2023

(54) METHOD FOR BUILDING FARMLAND ECOSYSTEM WITH MULTIPLE MUTUAL-BENEFIT SPECIES IN MULTIPLE HABITATS

(71) Applicant: Agricultural Environmental Resources Research Institute, Yunnan Academy of Agricultural Sciences, Kunming (CN)

(72) Inventors: Baokun Lei, Yunnan (CN); Yongbo Xu, Yunnan (CN); Anqiang Chen, Yunnan (CN); Yanting Mao, Yunnan (CN); Shufang Guo, Yunnan (CN); Fengchao Ping, Yunnan (CN); Haocheng Wang, Yunnan (CN); Xiaobing Liu, Yunnan (CN); Fan Gao, Yunnan (CN); Guimei Jin, Yunnan (CN); Yanxian Yang, Yunnan (CN)

(73) Assignee: Agricultural Environmental Resources Research Institute, Yunnan Academy of Agricultural Sciences, Kunming (CN)

( * ) Notice: Subject to any disclaimer, the term of this patent is extended or adjusted under 35 U.S.C. 154(b) by 245 days.

(21) Appl. No.: 17/395,731

(22) Filed: Aug. 6, 2021

(65) Prior Publication Data

US 2022/0110266 A1 Apr. 14, 2022

(30) Foreign Application Priority Data

Oct. 9, 2020 (CN) .......................... 202011071234.7

(51) Int. Cl.
*A01G 7/00* (2006.01)
*A01G 22/00* (2018.01)
(Continued)

(52) U.S. Cl.
CPC ............. *A01G 7/00* (2013.01); *A01G 17/005* (2013.01); *A01G 22/00* (2018.02); *A01K 61/00* (2013.01);
(Continued)

(58) Field of Classification Search
CPC ........ A01G 7/00; A01G 22/00; A01G 17/005; A01K 61/00; A01K 61/10; A01K 61/70;
(Continued)

(56) References Cited

U.S. PATENT DOCUMENTS 9,402,378 B2 * 8/2016 Zhang ....................... A01K 5/00
2011/0209404 A1 * 9/2011 Scott ......................... A01G 7/00
62/264
(Continued)

FOREIGN PATENT DOCUMENTS

CN 104365556 A * 2/2015 ......... A01K 67/0332
CN 104396825 A * 3/2015 ............. A01C 21/00
(Continued)

*Primary Examiner* — Ebony E Evans
(74) *Attorney, Agent, or Firm* — Renner, Kenner, Greive, Bobak, Taylor & Weber

(57) ABSTRACT

A method for building a farmland ecosystem with multiple mutual-benefit species in multiple habitats is provided. The method includes: marking out an ecological field plot for planting crops in a farmland, arranging one to three earthworm breeding strip stack(s) at equal intervals, and marking out different planting areas; digging an ecological field ditch surrounding a periphery of the ecological field plot, and planting aquatic plants and breeding aquatic animals in the ecological field ditch; surrounding a periphery of the ecological field ditch with an ecological wide ridge, planting forage plants on a ridge surface of the ecological wide ridge, and planting arbors on an outer side of the ecological wide ridge; and arranging an ecological pond on a drainage side
(Continued)

of a hole, wherein aquatic plants are planted in the ecological pond, and crustaceans are bred in the ecological pond.

20 Claims, 1 Drawing Sheet

(51) Int. Cl.
    *A01G 17/00*     (2006.01)
    *A01K 61/00*     (2017.01)
    *A01K 67/02*     (2006.01)
    *A01K 67/033*    (2006.01)
    *E02B 1/00*      (2006.01)

(52) U.S. Cl.
    CPC .......... *A01K 67/02* (2013.01); *A01K 67/0332* (2013.01); *E02B 1/00* (2013.01)

(58) Field of Classification Search
    CPC . A01K 67/02; A01K 67/0332; A01K 67/0335
    See application file for complete search history.

(56) References Cited

U.S. PATENT DOCUMENTS

| | | | | |
|---|---|---|---|---|
| 2020/0063388 A1* | 2/2020 | Rodriguez Larreta | . | C02F 3/327 |
| 2022/0174916 A1* | 6/2022 | Wang | ..................... | A01K 61/10 |

FOREIGN PATENT DOCUMENTS

| | | | | |
|---|---|---|---|---|
| CN | 106538465 A | * | 3/2017 | |
| CN | 107487854 A | * | 12/2017 | ............ A01G 22/00 |
| CN | 109673401 A | * | 4/2019 | |
| EP | 1112680 B1 | * | 3/2005 | ............ A01G 31/00 |

* cited by examiner

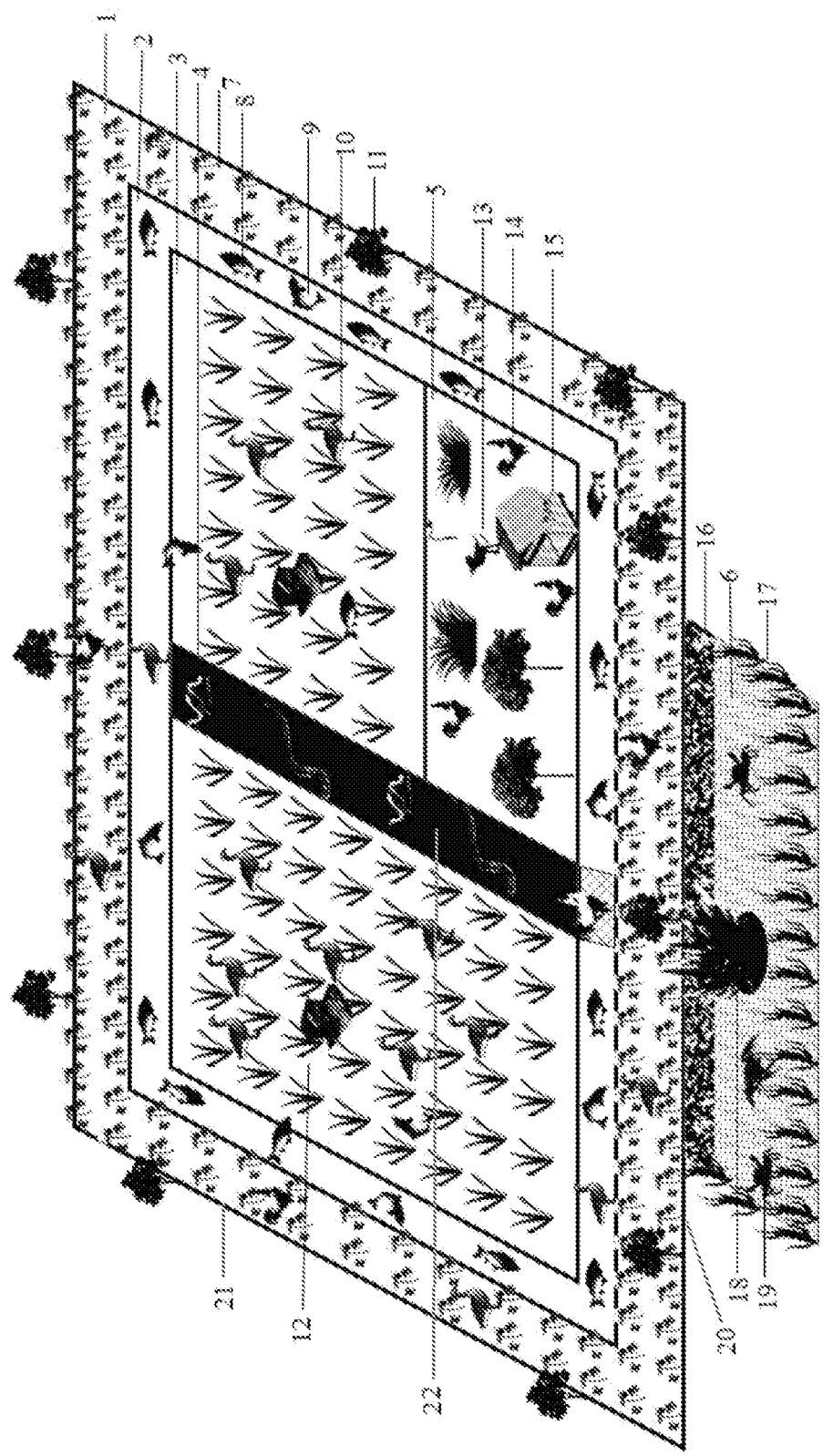

METHOD FOR BUILDING FARMLAND ECOSYSTEM WITH MULTIPLE MUTUAL-BENEFIT SPECIES IN MULTIPLE HABITATS

CROSS REFERENCE TO RELATED APPLICATION(S)

This patent application claims the benefit and priority of Chinese Patent Application No. 202011071234.7, filed on Oct. 9, 2020, the disclosure of which is incorporated by reference herein in its entirety as part of the present application.

TECHNICAL FIELD

The present disclosure belongs to the technical field of agroecological environment, and in particular relates to a method for building a farmland ecosystem with multiple mutual-benefit species in multiple habitats.

BACKGROUND ART

A farmland ecosystem refers to a complex in which human beings use mutual relations between biological environment and non-biological environment and among biological populations to convert energy and circulate materials through a reasonable ecological structure and an efficient ecological function in a crop-centered farmland, and produce materials according to needs of human society. The farmland ecosystem is a major subsystem of an agricultural ecosystem and an ecosystem domesticated by human beings. Accordingly, the farmland ecosystem is not only restricted by natural ecological laws of nature, but also affected by social and economic laws of human activities.

Grain output is increasingly dependent on chemical fertilizer, so chemical fertilizer and pesticides are widely used in farmlands. In the meantime, the farmland ecosystem is severely polluted during booming in industry, rendering all living things in the system threatened, and grain quality and output affected. The resourceful utilization rate of waste in the system is low, and an agricultural output value is low. Therefore, the existing farmland ecosystem needs to be improved to transform agriculture from high input, high pollution, low efficiency and low output value to low input, low pollution, high efficiency and high output value.

SUMMARY

In order to solve the problems in the background art, the present disclosure provides a method for building a farmland ecosystem with multiple mutual-benefit species in multiple habitats, which improves the resource utilization efficiency of the farmland ecosystem to the maximum extent, greatly reduces application of chemical fertilizer and pesticides, and reduces environmental damage and pollution. By means of different ecological niches of living things, a beneficial ecological service function is brought into play such that species in the farmland ecosystem can live in a suitable farmland microenvironment, competition for the same living space in the same place is avoided, and harmonious coexistence among the living things is realized; and food with high quality and a higher grain output value are provided.

In order to achieve the above purposes, the present disclosure employs the following technical solution:

the method for building a farmland ecosystem with multiple mutual-benefit species in multiple habitats includes:

step 1, mark out an ecological field plot 3 for planting crops in a farmland, arrange 1-3 earthworm breeding strip stacks 4 at equal intervals according to a length of the ecological field plot 3, and mark out different planting areas of the ecological field plot 3 by the earthworm breeding strip stack 4;

step 2, dig an ecological field ditch 2 surrounding the ecological field plot 3 at a periphery of the ecological field plot 3, and plant aquatic plants and breed aquatic animals in the ecological field ditch 2;

step 3, surrounding the ecological field ditch 2 with an ecological wide ridge 1 at a periphery of the ecological field ditch 2, plant forage plants 7 on a ridge surface of the ecological wide ridge 1, and plant arbors 11 on an outer side of the ecological wide ridge 1, so as to form a field forest network; and step 4, arrange an ecological pond 6 on a drainage side 20 of a whole formed by the ecological field plot 3, the ecological field ditch 2 and the ecological wide ridge 1, where aquatic plants 17 are planted in the ecological pond 6, and crustaceans 19 are bred in the ecological pond 6.

Further, in the step 1, a terrestrial space 5 for breeding poultry is marked out in one area, marked out by the earthworm breeding strip stack 4, of the ecological field plot 3.

Further, poultry suitable for living on land is bred in the terrestrial space 5, plants such as arbors, shrubs and grass are planted in the terrestrial space 5, and a poultry house 15 is built in the terrestrial space 5.

Further, ducks 10 are bred on the ecological field plot 3, a duck house 12 is arranged in a middle of each area, marked out by the earthworm breeding strip stack 4, of the ecological field plot 3, and an escape-proof fence 21 is arranged on a periphery of the ecological wide ridge 1.

Further, a width of the ecological wide ridge 1 is no less than 1 m.

Further, no more than ten arbors 11 are planted per mu of farmland.

Further, the ecological field ditch 2 is a seasonal shallow ditch or a permanent deep ditch, and a width of the ecological field ditch 2 is no less than 1 m; when the ecological field ditch 2 is the seasonal shallow ditch, a ditch depth is no less than 0.5 m; and when the ecological field ditch 2 is the permanent deep ditch, the ditch depth is no less than 1 m.

Further, the earthworm breeding strip stack 4 is in a strip shape and is higher than a surface of the ecological field plot 3, and a spray irrigation or drip irrigation apparatus for replenishing water for earthworm breeding is arranged on the earthworm breeding strip stack 4; and a plastic film or a rain shelter 22 that is used for guaranteeing suitable humidity for growth of earthworms is arranged on a surface of the earthworm breeding strip stack 4.

Further, an ecological island 18 is arranged in a center of the ecological pond 6, plants such as arbors, shrubs and grass are planted on the ecological island 18, and the aquatic animals bred in the ecological pond 6 are the crustaceans 19.

Further, a connection band 16 is arranged at a joint between the ecological pond 6 and the ecological wide ridge 1, and a filling material for adsorbing nitrogen and phosphorus in farmland tail water is arranged in the connection band 16.

The present disclosure has the beneficial effects:

the present disclosure improves the resource utilization efficiency of the farmland ecosystem to the maximum extent, greatly reduces application of the chemical fertilizer and the pesticides, and reduces the environmental damage and pollution; and by means of different ecological niches of the living things, the beneficial ecological service function is brought into play such that species in the farmland ecosystem can live in the suitable farmland microenvironment, the competition for the same living space in the same place is avoided, and the harmonious coexistence among the living things is realized; and the food with high quality and the higher grain output value are provided.

BRIEF DESCRIPTION OF THE DRAWINGS

FIG. 1 is a structural schematic diagram of the present disclosure.

DETAILED DESCRIPTION OF THE EMBODIMENTS

The technical solutions in the embodiments of the present disclosure will be clearly and completely described below with reference to the embodiments and accompanying drawings of the present disclosure. Apparently, the described embodiments are merely a part rather than all of the embodiments of the present disclosure. All other embodiments obtained by a person of ordinary skill in the art on the basis of the embodiments of the present disclosure without creative efforts shall fall within the protection scope of the present disclosure.

A method for building a farmland ecosystem with multiple mutual-benefit species in multiple habitats includes:

step 1, mark out an ecological field plot 3 for planting crops in a farmland, arrange 1-3 earthworm breeding strip stacks 4 at equal intervals according to a length of the ecological field plot 3, and mark out different planting areas of the ecological field plot 3 by the earthworm breeding strip stack 4.

The earthworm breeding strip stack 4 is arranged in a middle of the ecological field plot 3, in a strip shape and higher than a surface of the ecological field plot 3, and a spray irrigation or drip irrigation apparatus for replenishing water for earthworm breeding is arranged on the earthworm breeding strip stack 4; and a plastic film or a rain shelter 22 that is used for guaranteeing suitable humidity for growth of earthworms is arranged on a surface of the earthworm breeding strip stack 4. The earthworms bred on the earthworm breeding strip stack 4 may dig soil on the ecological field plot 3 such that the soil may be loosened, more oxygen may permeate through the soil, and then the growth of plants may be promoted. Meanwhile, the earthworms may degrade some pollutants such that the soil may be improved.

A terrestrial space 5 for breeding poultry is marked out in one area, marked out by the earthworm breeding strip stack 4, of the ecological field plot 3. A poultry house 15 is built in the terrestrial space 5, poultry suitable for living on land is bred in the terrestrial space 5, and meanwhile, plants such as arbors, shrubs and grass are planted in the terrestrial space 5, such that a terrestrial ecological space is built and becomes a good habitat space for the terrestrial poultry. 2-3 geese 13 are bred in the terrestrial space to serve as animals with nursing functions, so as to avoid damage to the other living things in the farmland ecosystem caused by outside animals such as dogs and wild birds. The terrestrial poultry mainly take the terrestrial space 5 as the habitat space, and excreta of the terrestrial poultry flows into the ecological field plot 3 to serve as fertilizer and nutrient sources of crops. The poultry house 15 is arranged to serve as a shelter for the poultry. The terrestrial space 5 may serve as a temporary management and transfer area and an operation space at the same time for aquatic poultry during harvesting.

Ducks 10 are bred on the ecological field plot 3, a duck house 12 is arranged in a middle of each planting area, marked out by the earthworm breeding strip stack 4, of the ecological field plot 3, and an escape-proof fence 21 is arranged on a periphery of the ecological wide ridge 1. In the present disclosure, dry ducks are preferably bred, and due to a nature of less inactiveness of the dry duck, the poultry is prevented from escaping from the ecological field plot 3, so as to facilitate management. The water ducks may be also bred, and if the water ducks are bred, escape-proof work needs to be well done. The duck house 12 is arranged in the middle of each planting area of the ecological field plot 3 such that excreta of the ducks may be effectively prevented from flowing out, and the excreta of the ducks may be conveniently diffused to a periphery of the duck house 12, so as to provide nutrients for the crops.

Step 2: dig an ecological field ditch 2 surrounding the ecological field plot 3 at a periphery of the ecological field plot 3, and plant aquatic plants and breed aquatic animals in the ecological field ditch 2.

The ecological field ditch 2 is a seasonal shallow ditch or a permanent deep ditch, and a width of the ecological field ditch 2 is no less than 1 m; when the ecological field ditch 2 is the seasonal shallow ditch, a ditch depth is no less than 0.5 m; when the ecological field ditch 2 is the permanent deep ditch, the ditch depth is no less than 1 m; and aquatic plants are planted in the ecological field ditch 2, and fishes are bred in the ecological field ditch 2. The ecological field ditch 2, on the one hand, is a living habitat of fishes and the like, and on the other hand, is a refuge pond for the fishes under a condition of water shortage. Moreover, the fishes bred in the ecological field ditch 2 may freely shuttle and swim between the ecological field ditch 2 and the ecological field plot 3, such that material and energy flow of the whole farmland system is driven; and the ecological field ditch 2 may guarantee long-term water storage such that the influence on crop planting and the death of the fishes due to water shortage of the ecological field plot 3 may be avoided. In order to give full play to maximum ecological benefits, different types of fishes are bred, in a mixed manner, in the ecological field ditch 2, which include small-sized omnivorous fishes 8 (such *crucians*) and large-sized omnivorous fishes 9 (such as carps). Under a condition that a growth period in a farmland is short, fish fry with large fry age may be selected and guaranteed to rapidly grow in a short period. Adult fishes bred in a pond may be also selected for purification and fosterage, so as to improve the quality of fish products. The ecological field ditch 2 may be designed as either the permanent deep ditch or the seasonal shallow ditch. The depth of the permanent deep ditch is no less than 1 m, and a width thereof is no less than 1 m; aquatic plants (including the submerged plants and the emergent plants) are planted in the ditch; and water is permanently stored in the ditch, so as to realize annual aquaculture. The depth of the seasonal shallow ditch is designed to be no less than 0.5 m, and a width thereof is designed to be no less than 1 m; a ditch wall is properly reinforced; and water storage situations in the ditch change with the change of plant planting seasons, specifically, water storage is carried out in the water farming seasons, and drying is carried out in the dry farming seasons.

In the present disclosure, the ducks eat weeds in a living process so as to remove the weeds, and meanwhile also eat and kill harmful insects, such that ventilation and light transmission among the crops are increased, the dissolved oxygen amount of water of the ecological field plot 3 is increased, and the growth of the crops and the fishes is promoted. Meanwhile, the crops also provide a habitat and a shelter for the ducks, so as to achieve a mutual benefit and win-win result. The ecological field plot 3 is also a living space, a foraging space and a sports field of the fishes. The fishes and the poultry may freely shuttle between the ecological field plot 3 and the ecological field ditch, such that the material and energy flow of the whole farmland system is driven.

Meanwhile, the earthworms bred on the earthworm breeding strip stack 4 may provide protein food with high quality for the fishes and the poultry, and livestock excrement converted by the earthworms is returned to the field to serve as the fertilizer with high quality for the crops and improve the soil, such that the soil is healthier and better in quality, and a good way is provided for resourceful utilization of the livestock excrement.

Step 3: surrounding the ecological field ditch 2 with an ecological wide ridge 1 at a periphery of the ecological field ditch 2, plant forage plants 7 on a ridge surface of the ecological wide ridge 1, and plant arbors 11 on an outer side of the ecological wide ridge 1, so as to form a field forest network.

The ecological wide ridge 1 is located at a periphery of the whole farmland ecosystem; a width of the ecological wide ridge is relatively wide, and a width thereof is no less than 1 m; sufficient ecological space for plant growth and living thing inhabitation may be provided; and forage plants 7 (such as leguminous forage) are planted on the ecological wide ridge 1, where the forage plants 7 provide food and nutrients for living things in the farmland ecosystem after being harvested, and meanwhile provide a comfortable land habitat for the living things. Arbors 11 are planted on an outermost side of the ecological wide ridge 1 to form a field forest network, such that shading, wind-proof and other functions are provided for the farmland system, microclimates of the farmland are improved, and soil erosion and quicksand harm are prevented. The arbors 11 should not be planted too much, if too much arbors are planted, excessive shading will be caused to affect lighting of the farmland system, and too many root systems of the arbors will compete for nutrients and water in the soil; and generally, it is appropriate to plant no more than 10 arbors per mu of farmland. When necessary, an escape-proof fence 21 may be additionally arranged at a periphery of the ecological wide ridge 1, so as to prevent the bred poultry from escaping.

In the present disclosure, the terrestrial poultry may take the terrestrial space 5 as the habitat space, and may also take the ecological wide ridge 1 and the earthworm breeding strip stack 4 as living spaces for foraging, living, moving and the like. Meanwhile, the biological field ditch 2 is located at an inner circle of the ecological wide ridge 1, and the ecological field ditch 2 is closely connected to the ecological wide ridge 1 such that the biological terrestrial space may be converted into an aquatic space.

Step 4: arrange an ecological pond 6 on a drainage side 20 of a whole formed by the ecological field plot 3, the ecological field ditch 2 and the ecological wide ridge 1, where aquatic plants 17 are planted in the ecological pond 6, and crustaceans 19 are bred in the ecological pond 6.

The ecological pond 6 is located on the drainage side of the farmland, and farmland tail water flows into the ecological pond. Living things are distributed in the ecological pond 6, the aquatic plants 17 are planted, crustaceans 19 are bred and the crustaceans 19 are crabs, lobsters and the like, the ducks may also enter the ecological pond, the fishes do not enter the ecological pond 6 due to strong competition with the crustaceans 19, and the crustaceans 19 do not enter the biological field ditch 2 and the ecological field plot 3, such that space isolation among different animals is carried out. An ecological island 18 is arranged in a center of the ecological pond 6, plants such as arbors, shrubs and grass are planted on the ecological island 18, so as to provide a shelter space and a living space for aquatic living things. Meanwhile, the ecological pond 18 serves as a temporary management and transfer area and an operation space at the same time for the fishes during harvesting. The farmland tail water, rainwater and the like accumulated in the ecological pond 18 are pumped back to the ecological field plot 3 by a water pump for recycling, such that the recycling efficiency of water resources and nutrient resources in the water is improved.

In the present disclosure, a connection band 16 is arranged at a joint between the ecological pond 6 and the ecological wide ridge 1, and a filling material for adsorbing nitrogen and phosphorus in the farmland tail water is arranged in the connection band 16; and the tail water is filtered and purified and then flows into the ecological pond 16.

The present disclosure improves the resource utilization efficiency of the farmland ecosystem to the maximum extent, greatly reduces application of chemical fertilizer and pesticides, and reduces environmental damage and pollution. By means of different ecological niches of living things, a beneficial ecological service function is brought into play such that species in the farmland ecosystem can live in a suitable farmland microenvironment, competition for the same living space in the same place is avoided, and harmonious coexistence among the living things is realized; and food with high quality and a higher grain output value are provided, and a multi-win of "a rice bag, a vegetable basket and a money bag" is realized.

Lastly, the above preferred embodiments are only used to illustrate the technical solutions of the present disclosure but not to limit them. Although the present disclosure has been described in detail through the above preferred embodiments, a person skilled in the art should understand that various changes can be made in form and detail without departing from the scope defined by claims of the present disclosure.

What is claimed is:

1. A method for building a farmland ecosystem with multiple mutual-benefit species in multiple habitats, comprising the steps of:
   a. marking out an ecological field plot for planting crops in a farmland, arranging one to three earthworm breeding strip stack(s) at equal intervals according to a length of the ecological field plot, and marking out different planting areas of the ecological field plot by the earthworm breeding strip stack(s);
   b. digging an ecological field ditch surrounding the ecological field plot at a periphery of the ecological field plot, and planting aquatic plants and breeding aquatic animals in the ecological field ditch;
   c. surrounding the ecological field ditch with an ecological wide ridge at a periphery of the ecological field ditch, planting forage plants on a ridge surface of the ecological wide ridge, and planting arbors on an outer side of the ecological wide ridge, so as to form a field forest network; and
   d. arranging an ecological pond on a drainage side of a hole formed by the ecological field plot, the ecological field ditch and the ecological wide ridge, wherein aquatic plants are planted in the ecological pond, and crustaceans are bred in the ecological pond.

2. The method for building a farmland ecosystem with multiple mutual-benefit species in multiple habitats according to claim 1, wherein in the step a., a terrestrial space for breeding poultry is marked out in one area, marked out by the earthworm breeding strip stack(s), of the ecological field plot.

3. The method for building a farmland ecosystem with multiple mutual-benefit species in multiple habitats according to claim 2, wherein poultry suitable for living on land is bred in the terrestrial space, arbors, shrubs and grass are planted in the terrestrial space, and a poultry house is built in the terrestrial space.

4. The method for building a farmland ecosystem with multiple mutual-benefit species in multiple habitats according to claim 3, wherein the ecological field ditch is a seasonal shallow ditch or a permanent deep ditch, and a width of the ecological field ditch is no less than 1 m; when the ecological field ditch is the seasonal shallow ditch, a ditch depth is no less than 0.5 m; and when the ecological field ditch is the permanent deep ditch, the ditch depth is no less than 1 m.

5. The method for building a farmland ecosystem with multiple mutual-benefit species in multiple habitats according to claim 2, wherein ducks are bred on the ecological field plot, a duck house is arranged in a middle of each planting area, marked out by the earthworm breeding strip stack(s), of the ecological field plot, and an escape-proof fence is arranged on a periphery of the ecological wide ridge.

6. The method for building a farmland ecosystem with multiple mutual-benefit species in multiple habitats according to claim 5, wherein ducks are bred on the ecological field plot, a duck house is arranged in a middle of each planting area, marked out by the earthworm breeding strip stack(s), of the ecological field plot, and an escape-proof fence is arranged on a periphery of the ecological wide ridge.

7. The method for building a farmland ecosystem with multiple mutual-benefit species in multiple habitats according to claim 5, wherein a width of the ecological wide ridge is no less than 1 m.

8. The method for building a farmland ecosystem with multiple mutual-benefit species in multiple habitats according to claim 7, wherein no more than ten arbors are planted per mu of farmland.

9. The method for building a farmland ecosystem with multiple mutual-benefit species in multiple habitats according to claim 6, wherein a width of the ecological wide ridge is no less than 1 m.

10. The method for building a farmland ecosystem with multiple mutual-benefit species in multiple habitats according to claim 9, wherein no more than ten arbors are planted per mu of farmland.

11. The method for building a farmland ecosystem with multiple mutual-benefit species in multiple habitats according to claim 2, wherein the ecological field ditch is a seasonal shallow ditch or a permanent deep ditch, and a width of the ecological field ditch is no less than 1 m; when the ecological field ditch is the seasonal shallow ditch, a ditch depth is no less than 0.5 m; and when the ecological field ditch is the permanent deep ditch, the ditch depth is no less than 1 m.

12. The method for building a farmland ecosystem with multiple mutual-benefit species in multiple habitats according to claim 1, wherein ducks are bred on the ecological field plot, a duck house is arranged in a middle of each planting area, marked out by the earthworm breeding strip stack(s) of the ecological field plot, and an escape-proof fence is arranged on a periphery of the ecological wide ridge.

13. The method for building a farmland ecosystem with multiple mutual-benefit species in multiple habitats according to claim 12, wherein a width of the ecological wide ridge is no less than 1 m.

14. The method for building a farmland ecosystem with multiple mutual-benefit species in multiple habitats according to claim 13, wherein no more than ten arbors are planted per mu of farmland.

15. The method for building a farmland ecosystem with multiple mutual-benefit species in multiple habitats according to claim 14, wherein the ecological field ditch is a seasonal shallow ditch or a permanent deep ditch, and a width of the ecological field ditch is no less than 1 m; when the ecological field ditch is the seasonal shallow ditch, a ditch depth is no less than 0.5 m; and when the ecological field ditch is the permanent deep ditch, the ditch depth is no less than 1 m.

16. The method for building a farmland ecosystem with multiple mutual-benefit species in multiple habitats according to claim 13, wherein the ecological field ditch is a seasonal shallow ditch or a permanent deep ditch, and a width of the ecological field ditch is no less than 1 m; when the ecological field ditch is the seasonal shallow ditch, a ditch depth is no less than 0.5 m; and when the ecological field ditch is the permanent deep ditch, the ditch depth is no less than 1 m.

17. The method for building a farmland ecosystem with multiple mutual-benefit species in multiple habitats according to claim 1, wherein the ecological field ditch is a seasonal shallow ditch or a permanent deep ditch, and a width of the ecological field ditch is no less than 1 m; when the ecological field ditch is the seasonal shallow ditch, a ditch depth is no less than 0.5 m; and when the ecological field ditch is the permanent deep ditch, the ditch depth is no less than 1 m.

18. The method for building a farmland ecosystem with multiple mutual-benefit species in multiple habitats according to claim 1, wherein the earthworm breeding strip stack(s) is/are in a strip shape and is higher than a surface of the ecological field plot, and a spray irrigation or drip irrigation apparatus for replenishing water for earthworm breeding is arranged on the earthworm breeding strip stack(s); and a plastic film or a rain shelter that is used for guaranteeing suitable humidity for growth of earthworms is arranged on a surface of the earthworm breeding strip stack(s).

19. The method for building a farmland ecosystem with multiple mutual-benefit species in multiple habitats according to claim 1, wherein an ecological island is arranged in a center of the ecological pond, seed arbors, shrubs and grass are on the ecological island, and the aquatic animals bred in the ecological pond are the crustaceans.

20. The method for building a farmland ecosystem with multiple mutual-benefit species in multiple habitats according to claim 19, wherein a connection band is arranged at a joint between the ecological pond and the ecological wide ridge, and a filling material for adsorbing nitrogen and phosphorus in farmland tail water is arranged in the connection band.

* * * * *